US00PP32320P3

(12) United States Plant Patent
Koekkoek

(10) Patent No.: US PP32,320 P3
(45) Date of Patent: Oct. 13, 2020

(54) CARNATION PLANT NAMED 'HILAGAS'

(50) Latin Name: ***Dianthus* L.**
Varietal Denomination: Hilagas

(71) Applicant: Arthur N. J. Koekkoek, Alkmaar (NL)

(72) Inventor: Arthur N. J. Koekkoek, Alkmaar (NL)

(73) Assignee: HILVERDA KOOIJ B.V., De Kwakel (NL)

( * ) Notice: Subject to any disclaimer, the term of this patent is extended or adjusted under 35 U.S.C. 154(b) by 0 days.

(21) Appl. No.: 16/501,652

(22) Filed: May 16, 2019

(65) Prior Publication Data

US 2019/0357401 P1 Nov. 21, 2019

Related U.S. Application Data

(60) Provisional application No. 62/762,743, filed on May 17, 2018.

(51) Int. Cl.
*A01H 5/02* (2018.01)
*A01H 6/30* (2018.01)

(52) U.S. Cl.
USPC ..... Plt./278
CPC ..... *A01H 6/305* (2018.05)

(58) Field of Classification Search
USPC ..... Plt./263.1, 272, 278
See application file for complete search history.

(56) References Cited

PUBLICATIONS

HilverdaKooij plant technology: Pt & Bedding Plants 2017-2018. http://www.tecniplant.cat/catalogos/hilverdakooij-potplant.pdf. 3 pages (Year: 2017).*

* cited by examiner

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of Carnation plant named 'Hilagas', characterized by its compact, upright to broadly spreading and uniformly mounding plant habit; freely branching habit; early and freely flowering habit; red-colored double flowers; and good container and garden performance.

1 Drawing Sheet

Botanical designation: *Dianthus* L.
Cultivar denomination: 'HILAGAS'.

BACKGROUND OF THE INVENTION

The present invention relates to a new and distinct cultivar of Carnation plant, botanically known as *Dianthus* L., grown commercially as a container plant and hereinafter referred to by the name 'Hilagas'.

The new Carnation plant is a product of a planned breeding program conducted by the Inventor in De Kwakel, The Netherlands. The objective of the breeding program is to create new container Carnation plants with numerous attractive flowers.

The new Carnation plant originated from a cross-pollination made by the Inventor in De Kwakel, The Netherlands in May, 2012 of a proprietary selection of *Dianthus* L. identified as code number A86099-27, not patented, as the female, or seed, parent with *Dianthus* L. 'Feline', not patented, as the male, or pollen, parent. The new Carnation plant was discovered and selected by the Inventor as a single flowering plant from within the progeny of the stated cross-pollination in a controlled greenhouse environment in De Kwakel, The Netherlands in June, 2013.

Asexual reproduction of the new Carnation plant by terminal cuttings propagated in a controlled greenhouse environment in De Kwakel, The Netherlands since March, 2014 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilagas'. These characteristics in combination distinguish 'Hilagas' as a new and distinct Carnation plant:

1. Compact, upright to broadly spreading and uniformly mounding plant habit.
2. Freely branching habit.
3. Early and freely flowering habit.
4. Red-colored double flowers.
5. Good container and garden performance.

Plants of the new Carnation differ primarily from plants of the female parent selection in the following characteristics:

1. Plants of the new Carnation flower later than plants of the female parent selection.
2. Plants of the new Carnation produce fewer flowers per lateral branch than plants of the female parent selection.

3. Flower petals of plants of the new Carnation flower are not as round as flower petals of plants of the female parent selection.
4. Flowers of plants of the new Carnation are red in color whereas flowers of plants of the female parent selection are cherry red in color.

Plants of the new Carnation differ primarily from plants of the male parent, 'Feline', in the following characteristics:

1. Plants of the new Carnation are more compact than plants of 'Feline'.
2. Plants of the new Carnation have larger flowers than plants of 'Feline'.
3. Flower petals of plants of the new Carnation have fewer incisions than flower petals of plants of 'Feline'.
4. Flowers of plants of the new Carnation are red in color whereas flowers of plants of 'Feline' are cherry red in color.

Plants of the new Carnation also can be compared to plants of *Dianthus caryophyllus* 'Hilreal', disclosed in U.S. Plant Pat. No. 22,408. In side-by-side comparisons, plants of the new Carnation differ primarily from plants of 'Hilreal' in the following characteristics:

1. Plants of the new Carnation grow slightly slower than plants of 'Hilreal'.
2. Flower petals of plants of the new Carnation are not as deeply incised as flower petals of plants of 'Hilreal'.
3. Flowers of plants of the new Carnation are darker red in color than flowers of plants of 'Hilreal'.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant. The photograph comprises a side perspective view of a typical flowering plant of 'Hilagas' grown in a container.

DETAILED BOTANICAL DESCRIPTION

Plants used in the aforementioned photograph and following observations and measurements were grown during the spring in 10.5-cm containers in a glass-covered greenhouse in De Kwakel, The Netherlands and under cultural practices typical of commercial container Carnation production. During the production of the plants, day temperatures ranged from 16° C. to 20° C. and night temperatures ranged from 16° C. to 18° C. Plants used for the photograph and description were 13 weeks from planting and were pinched one time at the time of planting. In the following description, color references are made to The Royal Horticultural Society Colour Chart, 2015 Edition, except where general terms of ordinary dictionary significance are used.

Botanical classification: *Dianthus caryophyllus* 'Hilagas'.

Parentage:

*Female, or seed, parent.*—Proprietary selection of *Dianthus* L. identified as code number A86099-27, not patented.

*Male, or pollen, parent.*—*Dianthus* L. 'Feline', not patented.

Propagation:

*Type.*—By terminal vegetative cuttings.

*Time to initiate roots, summer.*—About six days at temperatures ranging from 20° C. to 25° C.

*Time to initiate roots, winter.*—About eight days at temperatures about 18° C.

*Time to produce a rooted young plant, summer.*—About three weeks at temperatures ranging from 20° C. to 25° C.

*Time to produce a rooted young plant, winter.*—About five weeks at temperatures about 18° C.

*Root description.*—Medium in thickness, fibrous; white in color, actual color of the roots is dependent on substrate composition, water quality, fertilizer type and formulation, substrate temperature and physiological age of roots.

*Rooting habit.*—Moderate branching; medium density.

Plant description:

*Plant and growth habit.*—Herbaceous perennial, typically grown as a container plant; compact, uniformly mounding, upright to broadly spreading plant habit; moderately vigorous growth habit; slow to moderate growth rate.

*Plant height, soil level to top of foliar plane.*—About 12.7 cm.

*Plant height, soil level to top of floral plane.*—About 15.2 cm.

*Plant diameter or spread.*—About 21.4 cm.

*Lateral branches.*—Branching habit: Freely branching habit with about nine main (basal) stems; each main stem with about three lateral branches; pinching is not required, however, pinching will enhance lateral branch development. Length: About 10.7 cm. Diameter: About 3 mm. Internode length: About 2.1 cm. Strength: Strong. Aspect: Upright to about 50° from vertical. Texture and luster: Smooth, glabrous, waxy cuticle; matte. Color, developing: Close to 142D; at internodes, close to 145B. Color, developed: Close to NN137A; proximally, tinged with close to 184C; thin waxy cuticle, close to 189A.

Leaf description:

*Arrangement.*—Opposite, simple; sessile.

*Length.*—About 8 cm.

*Width.*—About 9 mm.

*Shape.*—Narrowly lanceolate; slightly carinate; slightly to moderately curled.

*Apex.*—Acute.

*Base.*—Attenuate; decurrent.

*Margin.*—Entire; not lobed.

*Texture and luster, upper and lower surfaces.*—Smooth, glabrous; slightly glossy.

*Venation pattern.*—Parallel.

*Color.*—Developing leaves, upper surface: Close to 144B. Developing leaves, lower surface: Close to 143C. Fully expanded leaves, upper surface: Close to NN137C; venation, close to NN137C. Fully expanded leaves, lower surface: Close to NN137C; venation, close to 143A.

Flower description:

*Flower form and flowering habit.*—Rotate double-type flowers arranged singly or in pairs; freely flowering habit with about 30 open flowers per plant at one time; flowers face mostly upright to slightly outwardly.

*Natural flowering season.*—Flowering is continuous from the spring to late summer in The Netherlands; plants begin flowering about 13 weeks after planting.

*Postproduction longevity*.—Flowers last about ten days on the plant; flowers not persistent.

*Fragrance*.—Moderately fragrant; clove-like, sweet and pleasant.

*Flower buds*.—Length: About 2.2 cm. Diameter: About 1.2 cm. Shape: Obovate. Texture and luster: Smooth, glabrous; slightly glossy. Color: Close to 137A; towards the base, close to 144B; petal apices, tinged with close to N45A.

*Flower diameter*.—About 4.8 cm.

*Flower depth*.—About 4 cm.

*Petals*.—Quantity and arrangement: About five petals arranged in a single whorl. Length: About 3.7 cm. Width: About 2.1 cm. Shape: Spatulate. Apex: Irregularly and finely dentate and praemorse. Base: Narrowly cuneate. Margin: Distally, irregularly and finely dentate; proximally, entire; moderately undulate. Texture and luster, upper and lower surfaces: Smooth, glabrous; velvety; matte. Color: When opening, upper and lower surfaces: Close to N45A; towards the base, close to 145B to 145C. Fully opened, upper surface: Close to N45B; towards the apex and margins, close to N45A; at the base, close to 145B to 145C; venation, similar to lamina colors; color does not change with development. Fully opened, lower surface: Close to N45D; towards the apex and the margins, close to N45A; at the base, close to 145B to 145C; venation, similar to lamina colors; colors do not change with development.

*Petaloids*.—Quantity and arrangement: About 30 petaloids arranged in about five whorls. Length: About 2.9 cm to 3.7 cm. Width: About 1.1 cm to 1.9 cm. Shape: Spatulate. Apex: Irregularly and finely dentate and praemorse. Base: Narrowly cuneate. Margin: Distally, irregularly and finely dentate; proximally, entire; moderately to highly undulate. Texture and luster, upper and lower surfaces: Smooth, glabrous; velvety; matte. Color: When opening, upper and lower surfaces: Close to N45A; towards the base, close to 145B to 145C. Fully opened, upper surface: Close to N45B; towards the apex and margins, close to N45A; at the base, close to 145B to 145C; venation, similar to lamina colors; color does not change with development. Fully opened, lower surface: Close to N45D; towards the apex and the margins, close to N45B; at the base, close to 145B to 145C; venation, similar to lamina colors; colors do not change with development.

*Sepals*.—Quantity and arrangement: Five sepals arranged in a single whorl; proximal 70% portion of the sepals are fused into a campanulate-shaped calyx. Calyx length: About 2.1 cm. Calyx diameter: About 1.3 cm. Sepal length: About 2.1 cm. Sepal width, at base of "free" portion: About 7 mm. Shape: Narrowly obovate. Apex: Broadly acute. Margin: Entire. Texture and luster, upper surface: Smooth, glabrous; slightly glossy. Texture and luster, lower surface: Smooth, glabrous; moderately glossy. Color: When opening, upper surface: Close to 147D; at the apex, flushed with close to 47D. When opening, lower surface: Close to 137B; towards the base, close to 145A; at the apex, flushed with close to 48B. Fully opened, upper surface: Close to 147D; at the apex, slightly flushed with close to 48B. Fully opened, lower surface: Close to 137A; towards the base, close to 144C; at the apex, flushed with close to 48C.

*Peduncles*.—Length: About 7 mm. Diameter: About 2.5 mm. Strength: Moderately strong. Aspect: About 20° from the stem axis. Texture and luster: Smooth, glabrous, waxy; matte. Color: Close to 137B and 143B; thin waxy layer, close to 189A.

*Reproductive organs*.—Stamens: Quantity: Typically one; significantly deformed. Filament length: About 0.8 cm to 1.3 cm. Filament color: Close to 157D. Anther size: About 0.5 mm by 1.5 mm. Anther shape: Irregularly oblong, deformed. Anther color: Close to 155C. Pollen: None observed to date. Pistils: Quantity: About one to three per flower. Pistil length: About 2.4 cm. Stigma diameter: About 1 mm. Stigma shape: Pointed, curved. Stigma color: Close to 53C. Style length: About 2.3 cm. Style color: Close to NN155C to NN155D and 53A. Ovary color: Close to 145B. Fruits and seeds: To date, fruit and seed development have not been observed on plants of the new Carnation.

Pathogen & pest resistance: To date, plants of the new Carnation have not been observed to be resistant to pathogens and pests common to Carnation plants.

Garden performance: Plants of the new Carnation have been observed to tolerate rain, wind, high temperatures about 35° C. and to be suitable for USDA Hardiness Zones 5 to 9.

It is claimed:

1. A new and distinct Carnation plant named 'Hilagas' as illustrated and described.

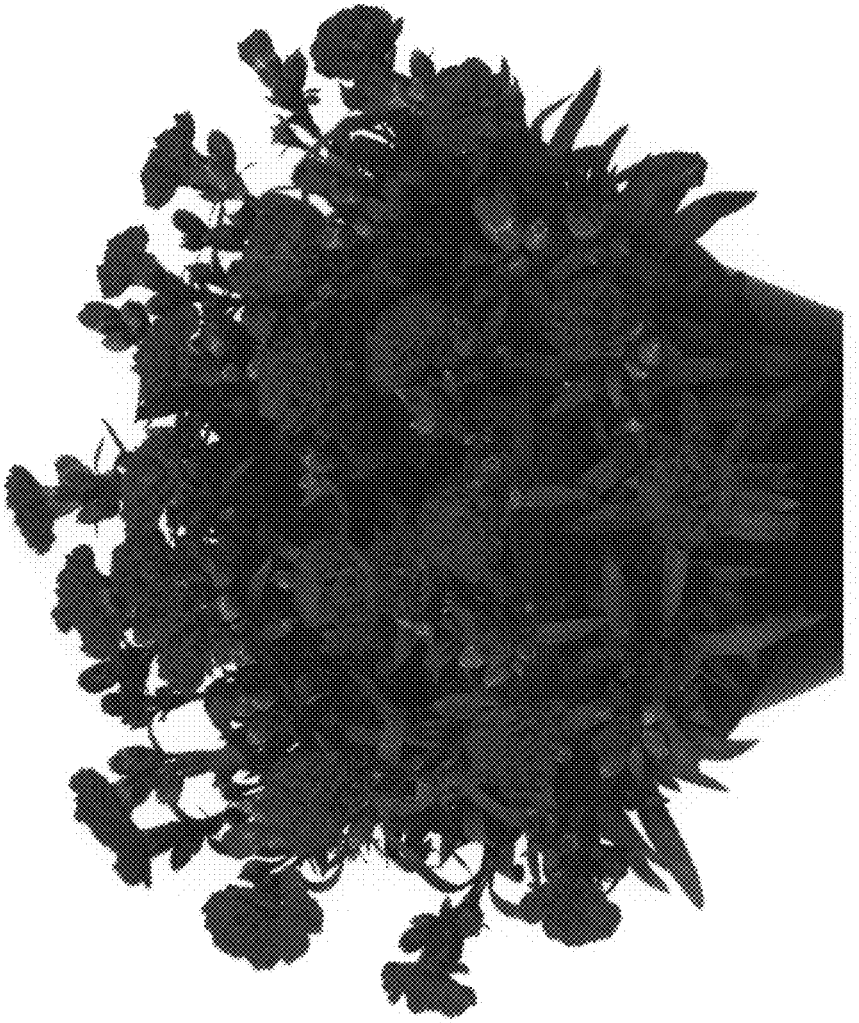

* * * * *